United States Patent [19]

Briggs et al.

[11] Patent Number: 4,711,887
[45] Date of Patent: Dec. 8, 1987

[54] HYDRAZINOPYRIDAZINE COMPOUNDS

[75] Inventors: Malcolm T. Briggs, Macclesfield; Robert I. Dowell, Congleton; Craig W. Thornber, Macclesfield, all of United Kingdom

[73] Assignee: Imperial Chemical Industries PLC, London, England

[21] Appl. No.: 479,913

[22] Filed: Mar. 28, 1983

[30] Foreign Application Priority Data

Apr. 23, 1982 [GB] United Kingdom ............... 8211760

[51] Int. Cl.$^4$ .................. C07D 237/20; A61K 31/50
[52] U.S. Cl. .................................. 514/247; 544/239
[58] Field of Search ............... 544/239, 237; 424/250; 514/247

[56] References Cited

U.S. PATENT DOCUMENTS

| 4,086,357 | 4/1978 | Large et al. | 544/224 |
| 4,324,788 | 4/1982 | Dorigotti et al. | 544/239 |
| 4,599,333 | 7/1986 | Yasuda et al. | 514/247 |

FOREIGN PATENT DOCUMENTS 0097202  1/1984  European Pat. Off.
57/108075  7/1982  Japan.

Primary Examiner—Nicholas S. Rizzo
Attorney, Agent, or Firm—Cushman, Darby & Cushman

[57] ABSTRACT

Hydrazinopyridiazine derivatives of the formula:

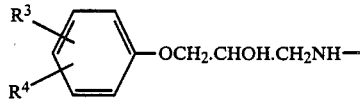

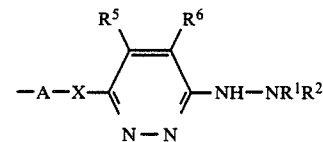

wherein A is alkylene, wherein either $R^1$ is hydrogen and $R^2$ is hydrogen, alkoxycarbonyl or aralkoxycarbonyl, or $R^1$ and $R^2$ together form alkylidene, aralkylidene, alkoxycarbonylalkylidene or aralkoxycarbonylalkylidene, wherein either $R^3$ and $R^4$, which may be the same or different, each is hydrogen, halogen, hydroxy, amino, nitro, trifluoromethyl, carbamoyl, cyano, alkyl, hydroxyalkyl, cycloalkyl, alkenyl, alkynyl, alkoxy, alkylthio, cycloalkoxy, alkenyloxy, alkynyloxy, alkanoyl, aryl, aryloxy or dialkylamino, or $R^3$ and $R^4$ together with the adjacent benzene ring form indanyl, 5,6,7,8-tetrahydronaphthyl, 5-oxo-5,6,7,8-tetrahydronaphthyl, indenyl, 5,8-dihydronaphthyl or naphthyl, wherein either $R^5$ and $R^6$, which may be the same or different, each is hydrogen or alkyl, or $R^5$ and $R^6$ together with the adjacent pyridazine ring form phthalazinyl, and wherein X is oxygen or —NHCO—, —NHCO—$A^1$— or —NHCO—$A^1$—O— wherein $A^1$ is alkylene, acid-addition salts thereof, processes for their manufacture and pharmaceutical composition containing them. The compounds possess antihypertensive activity.

10 Claims, No Drawings

HYDRAZINOPYRIDAZINE COMPOUNDS

This invention relates to nitrogenous compounds and more particularly it relates to novel hydrazinopyridazine derivatives which possess antihypertensive activity.

According to the invention there is provided a compound of the formula:

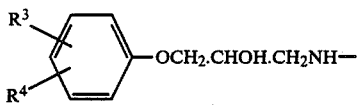

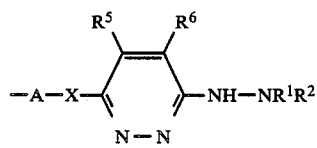

wherein A stands for an alkylene radical of from 2 to 6 carbon atoms, wherein either $R^1$ stands for hydrogen and $R^2$ stands for hydrogen or for an alkoxycarbonyl radical of from 2 to 6 carbon atoms or an aralkoxycarbonyl radical of from 8 to 12 carbon atoms, or $R^1$ and $R^2$ together form an alkylidene radical of from 2 to 6 carbon atoms or an aralkylidene radical of from 7 to 12 carbon atoms, or an alkoxycarbonyl or aralkoxycarbonylalkylidene radical of, respectively, from 4 to 10 or from 9 to 15 carbon atoms; wherein $R^3$ and $R^4$, which may be the same or different, each stands for a hydrogen or halogen atom, a hydroxy, amino, nitro, trifluoromethyl, carbamoyl or cyano radical, an alkyl, hydroxyalkyl, cyloalkyl, alkenyl, alkynyl, alkoxy, alkylthio, cycloalkoxy, alkenyloxy, alkynyloxy or alkanoyl radical each of up to 6 carbon atoms, or an aryl, aryloxy or dialkylamino radical each of up to 12 carbon atoms; or wherein $R^3$ and $R^4$ together form the trimethylene, tetramethylene, 1-oxotetramethylene, propylene, but-2-enylene or buta-1,3-dienylene radical such that together with the adjacent benzene ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein $R^5$ and $R^6$, which may be the same or different, each stands for a hydrogen atom or for an alkyl radical of up to 6 carbon atoms, or wherein $R^5$ and $R^6$ together form the buta-1,3-dienylene radical such that together with the adjacent pyridazine ring they form the phthalazinyl radical; and wherein X stands for the oxygen atom, or for an amido (—NH—CO—) radical, or for a radical of the formula —NH—CO—$A^1$— or —NHCO—$A^1$—O— wherein $A^1$ stands for an alkylene radical of up to 6 carbon atoms; or an acid-addition salt thereof.

It will be observed that the compound of the invention possesses at least one asymmetric carbon atom, namely, the carbon atom of the —CHOH— group in the alkanolamine sidechain, and it can therefore exist in racemic and optically-active forms. It is to be understood that this invention encompasses the racemic form of the compound and any optically-active form which possesses anti-hypertensive activity, it being a matter of common general knowledge how a racemic compound may be resolved into optically-active forms, and how the anti-hypertensive activity of these forms may be determined. It is further to be understood that any anti-hypertensive activity dependent upon β-adrenergic blocking activity usually predominates in that optically-active form which has the "S" absolute configuration of the said —CHOH— group.

A suitable value for the alkylene radical A is, for example, the ethylene, trimethylene, 1-methylethylene, 1,1-dimethylethylene or 1,2-dimethylethylene radical.

A suitable value for the alkylene radical $A^1$ is, for example, the methylene or ethylene racical.

A suitable value for $R^2$ when it stands for an alkoxycarbonyl or aralkoxycarbonyl radical is, for example, the methoxycarbonyl, ethoxycarbonyl or benzyloxycarbonyl radical.

A suitable value for the alkylidene, aralkylidene, alkoxyalkylidene or aralkoxyalkylidene radical formed by $R^1$ and $R^2$ together is, for example, the ethylidene, isopropylidene, benzylidene, 1-methyl-2-t-butoxycarbonylethylidene or 1-methyl-2-benzyloxycarbonylethylidene radical.

A suitable value for $R^3$ or $R^4$ when it stands for a halogen atom is, for example, the fluorine, chlorine, bromine or iodine atom.

A suitable value for $R^3$ or $R^4$ when it stands for an alkyl, hydroxyalkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, hydroxymethyl, 1-hydroxyethyl, cyclopropyl, cyclopentyl, allyl, ethynyl, methoxy, isopropoxy, methylthio, cyclopentyloxy, allyloxy, propargyloxy, formyl or acetyl radical.

A suitable value for $R^3$ or $R^4$ when it stands for an aryl, aryloxy or dialkylamino radical is, for example, the phenyl, phenoxy or dimethylamino radical.

A suitable value for $R^5$ or $R^6$ when it stands for an alkyl radical is, for example, the methyl or ethyl radical.

A suitable acid-addition salt of a compound of the invention is, for example, a salt derived from an inorganic acid, for example a hydrochloride, hydrobromide, phosphate or sulphate, or a salt derived from an organic acid, for example an oxalate, lactate, tartrate, acetate, silicylate, citrate, benzoate, β-naphthoate, adipate or 1,1-methylenebis-(2-hydroxy-3-naphthoate), or a salt derived from an acidic synthetic resin, for example a sulphonated polystyrene resin.

A preferred compound of the invention is a compound of the formula given above wherein A stands for the ethylene radical, wherein $R^1$ and $R^2$ both stand for hydrogen, wherein $R^3$ stands for a hydrogen or halogen atom or for an alkyl or alkoxy radical each of up to 3 carbon atoms in the orthoposition of the benzene ring and $R^4$ stands for hydrogen, wherein either $R^5$ and $R^6$ both stand for hydrogen atom or $R^5$ and $R^6$ together form the buta-1,3-dienylene radical, and wherein X stands for the oxygen atom or for a radical of the formula —NHCOCH$_2$O— or —NHCOCH$_2$—, or an acid-addition salt thereof.

Specific compounds of the invention are those hereinafter described in the Examples. Of these, preferred compounds are:

1-(2-tolyloxy)-3-β-(6-hydrazinopyridazin-3-yloxy)ethylamino-2-propanol and 1-(2-chlorophenoxy)-3-β-(4-hydrazinophthalazin-1-yloxyacetamido)ethylamino-2-propanol and the acid-addition salts thereof.

The compound of the invention may be manufactured by any chemical process known to be useful for the manufacture of chemically-analogous compounds. Thus, according to a further feature of the invention there is provided a process for the manufacture of a compound of the invention wherein $R^1$ stands for hydrogen which comprises the reaction of a pyridazine derivative of the formula:

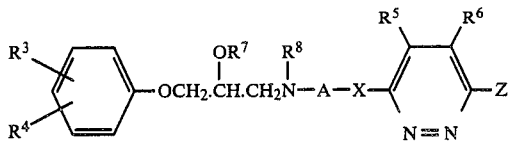

wherein A, $R^3$, $R^4$, $R^5$, $R^6$ and X have the meanings stated above, wherein $R^7$ and $R^8$, which may be the same or different, each stands for hydrogen or for a protecting group and wherein Z stands for a displaceable radical, with a hydrazine derivative of the formula $H_2NNHR^9$, wherein $R^9$ stands for a radical of the formula $R^2$ as defined above or for a protecting group, whereafter if one or more of $R^7$, $R^8$ and $R^9$ stands for a protecting group the one or more protecting groups are removed.

A suitable value for the displaceable radical Z is, for example, a halogen atom, for example the chlorine or bromine atom, or the mercapto radical, or an alkoxy or alkylthio radical each of up to 6 carbon atoms, for example the methoxy or methylthio radical, or an alkanesulphonyl radical of up to 6 carbon atoms or an arenesulphonyl radical of up to 10 carbon atoms, for example the methanesulphonyl or toluene-p-sulphonyl radical. Z is preferably the chlorine atom or the mercapto radical, and it is to be understood that when Z stands for the mercapto radical the starting material may exist in a thione structure of partial formula:

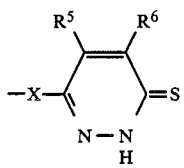

The protecting group $R^7$, $R^8$ or $R^9$, if present, is preferably a hydrogenolysable radical, for example an α-arylalkyl, α-arylalkoxycarbonyl or α-arylalkoxymethyl radical, for example the benzyl, benzyloxycarbonyl or benzyloxymethyl radical. It is to be understood that when $R^2$ is an aralkoxycarbonyl radical it may in fact be a radical removeable by hydrogenolysis, for example the benzyloxycarbonyl radical.

The hydrogenolysable protecting group $R^7$, $R^8$ or $R^9$ may be removed, for example, by catalytic hydrogenolysis, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The starting material for the process of the invention wherein X stands for the oxygen atom or for a radical of the formula —NHCO—$A^1$—O—, wherein $A^1$ has the meaning stated above, may be obtained by the reaction of a compound of the formula:

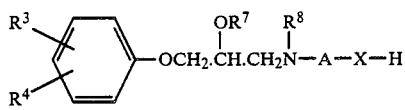

wherein A, $R^3$, $R^4$, $R^7$, $R^8$ and X have the meanings stated above, with a pyridazine derivative of the formula:

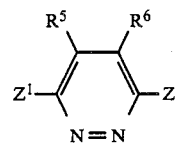

wherein $R^5$, $R^6$ and Z has the meaning stated above and wherein $Z^1$ stands for a displaceable radical which may be the same as or different from Z. $Z^1$ may be selected from the values stated above for Z.

The starting material for the process of the invention wherein X stands for a radical of the formula —NH-CO— or —NHCO—$A^1$—O—, wherein $A^1$ has the meaning stated above, may be obtained by the reaction of a compound of the formula:

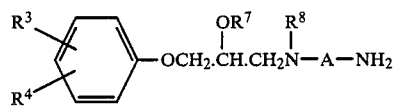

wherein A, $R^3$, $R^4$, $R^7$ and $R^8$ have the meanings stated above, with a compound of the formula:

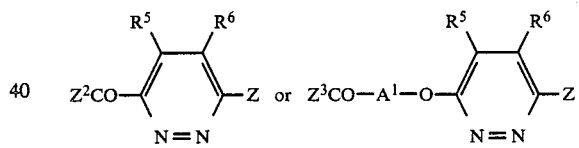

wherein $A^1$, $R^5$, $R^6$ and Z have the meanings stated above and wherein $Z^2$ and $Z^3$, which may be the same or different, each is a displaceable radical. $Z^2$ or $Z^3$ may be a halogen atom, for example the chlorine atom, or an alkoxy radical of up to 6 carbon atoms, for example the methoxy radical.

A compound of the invention wherein $R^1$ and $R^2$ together form an alkylidene, aralkylidene, alkoxyalkylidene or aralkoxyalkylidene radical may be obtained by the reaction of a compound of the invention wherein $R^1$ and $R^2$ both stand for hydrogen with an appropriate aldehyde or ketone, for example acetaldehyde, acetone, benzaldehyde, t-butyl 3-oxobutyrate or benzyl 3-oxobutyrate.

Optically-active enantiomorphs of the compound of the invention may be obtained by the resolution by conventional means of the corresponding racemic compound of the invention.

The said resolution may be carried out by reacting the racemic compound with an optically-active acid, followed by fractional crystallisation of the diastereoisomeric mixture of salts thus obtained from a diluent or solvent, for example ethanol, whereafter the optically-active compound is liberated from the salt by treatment with a base. A suitable optically-active acid is, for example, (+)- or (−)-O,O-di-p-toluoyltartaric acid or (−)-2,3:4,5-di-O-isopropylidene-2-keto-L-gulonic acid.

The resolution process may be facilitated by treating the partially resolved compound in free base form obtained after a single fractional crystallisation of the diastereoisomeric mixture of salts with a solubilising agent, for example a primary amine, for example allylamine, in a relatively non-polar diluent or solvent, for example petroleum ether.

The compound of the invention in free base form may be converted into an acid-addition salt thereof by reaction with an acid by conventional means.

As stated above, the compound of the invention possesses anti-hypertensive activity. This may be shown by demonstrating that the compound possesses β-adrenergic blocking activity, for it is well known that β-adrenergic blocking agents possess anti-hypertensive activity. Alternatively, the anti-hypertensive activity may be demonstrated by the lowering of blood pressure in a rat made hypertensive by treatment with deoxycorticosterone acetate, or by the lowering of peripheral resistance in the perfused hind limb of a dog, both these being standard test animal preparations used for the measurement of anti-hypertensive activity.

The compound of the invention may be administered to warm-blooded animals, including man, in the form of a pharmaceutical composition comprising as active ingredient at least one compound of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the compound of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorthiazide; other antihypertensive agents, for example reserpine, bethanidine and guanethidine; cardiac membrane stabilishing agents, for example quinidine; cardiotonic agents, for example digitalis preparations; other β-adrenergic blocking agents, for example propranolol and atenolol; and α-adrenergic blocking agents, for example phentolamine.

When used for the treatment of hypertension in man, it is expected that the compound of the invention would be given to man at a total oral dose of between 20 mg. and 1000 mg. daily, at doses spaced at 6–8 hourly intervals, or at an intravenous dose of between 1 mg. and 50 mg.

Preferred oral dosage forms are tablets or capsules containing between 10 and 100 mg., and preferably 10 mg. or 50 mg., of active ingredient. Preferred intravenous dosage forms are sterile aqueous solutions of the compound of the invention or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of 1-phenoxy-3-β-(6-chloropyridazin-3-yloxy)ethylamino-2-propanol (1.0 g.) and 95% hydrazine (7 ml.) is stirred and heated at 60° C. under an atmosphere of nitrogen for 4 hours and is then cooled. The excess of hydrazine is removed by evaporation under reduced pressure followed by azeotropic evaporation with ethanol, and the residue is shaken with a mixture of ethyl acetate and 10% aqueous acetic acid. The aqueous layer is basified with potassium carbonate and then extracted with chloroform, and the chloroform extract is dried and evaporated to dryness. A solution of hydrogen chloride in ethyl acetate is added to a solution of the residue in ethyl acetate, and the mixture is filtered. The residue is crystallised from isopropanol and there is thus obtained 1-phenoxy-3-β-(6-hydrazinopyridazin-3-yloxy)ethylamino-2-propanol dihydrochloride, m.p. 183°–185° C. (with decomposition).

The 1-phenoxy-3-β-(6-chloropyridazin-3-yloxy)ethylamino-2-propanol used as starting material may be obtained as follows:

A mixture of phenyl glycidyl ether (20 g.) and ethanolamine (40 ml.) is heated at 95°–100° C. for 3 hours, cooled, diluted with chloroform and then extracted with saturated aqueous sodium chloride solution. The organic layer is evaporated to dryness under reduced pressure and the residue is crystallised from ethyl acetate. There is thus obtained 1-phenoxy-3-α-hydroxyethylamino-2-propanol, m.p. 82°–84° C.

An 80% dispersion of sodium hydride in mineral oil (1.2 g.) is added portionwise during 15 minutes to a stirred suspension of the above compound (8.44 g.) in xylene (70 ml.), and the mixture is stirred for a further 10 minutes at laboratory temperature and is then cooled in an ice-bath 3,6-Dichloropyridazine (6.0 g.) is added and the mixture is stirred for 30 minutes at ice-bath temperature and then for 3 hours at laboratory temperature, and is then diluted with ethyl acetate and extracted with dilute aqueous hydrochloric acid. The acidic extract is basified with potassium carbonate and extracted with chloroform, and the chloroform extract is washed with aqueous sodium chloride solution, dried and evaporated to dryness. The residue is crystallised from a mixture of ethyl acetate and diethyl ether, and there is thus obtained 1-phenoxy-3-β-(6-chloropyridazin-3-yloxy)ethylamino-2-propanol, m.p. 104° C. (with decomposition).

The process described above is repeated except that 2-tolyl, 2-chlorophenyl or β-naphthyl glycidyl ether is used as initial starting material in place of phenyl glycidyl ether. There are thus obtained:

1-(2-tolyloxy)-3-β-(6-hydrazinopyridazin-3-yloxy)ethylamino-2-propanol dihydrochloride, m.p. 193°–195° C. (with decomposition); intermediates 1-(2-tolyloxy)-3-β-hydroxyethylamino-2-propanol, m.p. 70°–72° C. and 1-(2-tolyloxy)-3-β-(6-chloropyridazin-3-yloxy)ethylamino-2-propanol, m.p. 83°–85° C.;

1-(2-chlorophenoxy)-3-β-(6-hydrazinopyridazin-3-yloxy)ethylamino-2-propanol dihydrochloride, m.p. 160°–162° C. (with decomposition); intermediates 1-(2-chlorophenoxy)-3-β-hydroxyethylamino-2-propanol, m.p. 91°–92° C. and 1-(2-chlorophenoxy)3-β-(6-chloropyridazine-3-yloxy)ethylamino-2-propanol, m.p. 90°–93° C.; and 1-(β-naphthyloxy)-3-β-(6-hydrazinopyridazin-3-yloxy)ethylamino-2-propanol dihydrochloride dihydrate, m.p. 200°–203° C. (with decomposition); intermediates 1-(β-naphthyloxy)-3-β-hydroxyethylamino-2-propanol, m.p. 84°-86° C. and 1-(β-naphthyloxy)-3-β-(6-chloropyridazin-3-yloxy)ethylamino-2-propanol, m.p. 76°-79° C.

EXAMPLE 2

A mixture of 1-phenoxy-3-β-(6-chloropyridazin-3-yloxy)ethylamino-2-propanol hydrochloride (2.0 g.), benzyl carbazate (1.0 g.) and xylene (15 ml.) is stirred and heated at 110° C. for 3 hours, cooled and shaken with a mixture of ethyl acetate and dilute aqueous hydrochloric acid. The aqueous layer is separated and filtered and the filtrate is basified with aqueous sodium carbonate solution and then filtered. The solid product is crystallised from isopropanol and there is thus obtained 1-phenoxy-3-β-[6-(2-benzyloxycarbonylhydrazino)pyridazin-3-yloxy]ethylamino-2-propanol, m.p. 114°-116° C. (with decomposition).

The process described above is repeated except then ethyl carbazate is used in place of benzyl carbazate. There is thus obtained 1-phenoxy-3-β-[6-(2-ethoxycarbonylhydrazino)pyridazin-3-yloxy]ethylamino-2-propanol, m.p. 95°-98° C.

EXAMPLE 3

The process described in Example 2 is repeated using the appropriate 1-substituted-phenoxy-3-β-(6-chloropyridazin-3-yloxy)ethylamino-2-propanol as starting material, and there are thus obtained the compounds described in the following table:

| R³ | m.p. (°C.) |
|---|---|
| 3-methyl | 80-81 |
| 4-methyl | 73-75 |
| 2-allyl | 62-63 |
| 2-methoxy | 75-77 |
| 2-cyano | 94-95 |

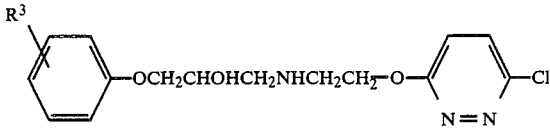

| R³ | m.p. (°C.) |
|---|---|
| 3-methyl | 96-97 |
| 4-methyl | 121-123 |
| 2-allyl | 71-73 |
| 2-methoxy | 103-105 |
| 2-cyano | 100 |

EXAMPLE 4

A mixture of 1-phenoxy-3-β-[6-(2-benzyloxycarbonylhydrazino)pyridazin-3-yloxy]ethylamino-2-propanol (0.3 g.), methanol (15 ml.), aqueous N-hydrochloric acid (0.66 ml.) and a 5% palladium-on-charcoal catalyst (0.05 g.) is shaken in an atmosphere of hydrogen at laboratory temperature and pressure for 16 hours and then filtered. Aqueous N-hydrochloric acid (0.66 ml.) is added to the filtrate, the mixture is evaporated to dryness and the residue is crystallised from isopropanol. There is thus obtained 1-phenoxy-3-β-(6-hydrazinopyridazin-3-yloxy)ethylamino-2-propanol dihydrochloride, m.p. 183°-185° C. (with decomposition).

The process described above is repeated using the appropriate benzyloxycarbonylhydrazino compound, described in Example 3, and there are thus obtained the compounds described in the following table:

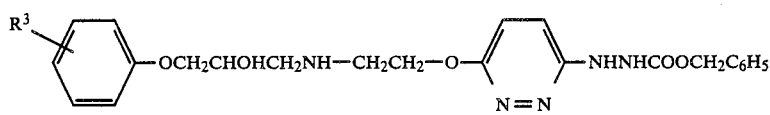

| R³ | | m.p. (°C.) |
|---|---|---|
| 2-methyl | dihydrochloride | 199-200 |
| 3-methyl | dihydrochloride | 192-194 |
| 4-methyl | dihydrochloride | 199-200 |
| 2-allyl | dihydrochloride | 181-183 |
| 2-methoxy | | 125-126 |
| 2-cyano | dihydrochloride | 198-200 |

The starting 6-chloropyridazin-3-yloxy compounds are obtained by a similar process to that described in the second and third paragraphs of Example 1, and are characterised as shown in the following tables:

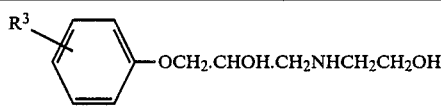

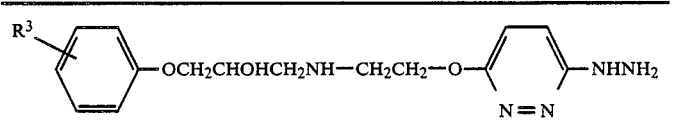

| R³ | | m.p. (°C.) |
|---|---|---|
| 2-methyl | dihydrochloride | 193-195(d) |
| 3-methyl | dihydrochloride | 191-193(d) |
| 4-methyl | dihydrochloride | 201-203(d) |
| 2-propyl* | dihydrochloride monohydrate | 186-188(d) |
| 2-methoxy | dihydrochloride hemihydrate | 155-157(d) |

-continued

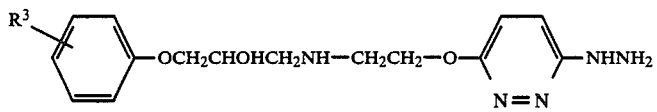

| R³ | m.p. (°C.) |
| --- | --- |
| 2-cyano | dihydrochloride monohydrate 151–154(d) |

*The corresponding 2-allylphenoxy compound is used as starting material, the allyl group being reduced to the propyl group during the reaction.

EXAMPLE 5

A mixture of 1-(2-chlorophenoxy)-3-β-(6-mercaptopyridazin-3-yloxyacetamido)ethylamino-2-propanol (0.7 g.), hydrazine hydrate (1.68 ml.) and ethanol (7 ml.) is heated under reflux for 2 hours under an atmosphere of nitrogen, and is the evaporated to dryness under reduced pressure. The excess of hydrazine is removed by azeotropic evaporation with ethanol and the residue is shaken with a mixture of butanol and water. The upper layer is separated and evaporated to dryness, the residue is triturated with isopropanol and the mixture is filtered. The solid product is crystallised from ethanol and there is thus obtained 1-(2-chlorophenoxy)-3-β-(6-hydrazinopyridazin-3-yloxyacetamido)ethylamino-2-propanol, m.p. 108°–110° C. (with decomposition).

The 1-(2-chlorophenoxy)-3-β-(6-mercaptopyridazin-3-yloxyacetamido)ethylamino-2-propanol used as starting material may be obtained as follows:

A mixture of ethyl 6-hydroxypyridazin-3-yloxyacetate (15 g.), phosphorus pentasulphide (16.8 g.) and dry tetrahydrofuran (350 ml.) is heated under reflux for 1 hour and filtered whilst hot. The solid residue is extracted with hot tetrahydrofuran and the combined filtrate and extract are evaporated to dryness. The residue is dissolved in chloroform, the mixture is filtered and the filtrate is added to a silica gel chromatography column made up in chloroform. The column is eluted with a 5% v/v solution of ethanol in chloroform and the eluate is evaporated to dryness. The residue is crystallised from isopropanol and there is thus obtained ethyl 6-mercaptopyridazine-3-yloxyacetate, m.p. 150°–151° C.

A mixture of the above compound (2.0 g.), 1-(2-chlorophenoxy)-3-β-aminoethylamino-2-propanol (4.5 g.) and n-butanol (25 ml.) is heated at 95°–100° C. under an atmosphere of nitrogen for 4 hours and is then diluted with water and evaporated to dryness under reduced pressure. The residue is dissolved in a mixture of aqueous N-hydrochloric acid and ethyl acetate and the organic layer is separated and extracted with aqueous N-hydrochloric acid. The combined acidic solutions are basified with potassium carbonate and the mixture is extracted three times with chloroform. The combined extracts are dried and evaporated to dryness and the residue is crystallised from ethanol. There is thus obtained 1-(2-chlorophenoxy)-3-β-(6-mercaptopyridazin-3-yloxyacetamido)ethylamino-2-propanol, m.p. 154°–156° C.

The process described above is repeated except that 1-(2-methoxyphenoxy)-3-β-aminoethylamino-2-propanol is used as intermediate. There is thus obtained 1-(2-methoxyphenoxy)-3-β-(6-hydrazinopyridazin-3-yloxyacetamido)ethylamino-2-propanol, m.p. 107°–110° C. (with decomposition), intermediate 1-(2-methoxyphenoxy)-3-β-(6-mercaptopyridazin-3-yloxyacetamido)ethylamino-2-propanol m.p. 147°–148° C.

The process described above is repeated except that 1-(2-tolyloxy)-3-β-aminoethylamino-2-propanol is used as intermediate. There is thus obtained 1-(2-tolyloxy)-3-β-(6-hydrazinopyridazin-3-yl-oxyacetamido)ethylamino-2-propanol, m.p. 120°–123° C. (with decomposition), intermediate 1-(2-tolyloxy)-3-β-(6-mercaptopyridazin-3-yloxyacetamido)ethylamino-2-propanol, m.p. 150°–152° C.

EXAMPLE 6

The process described in Example 5 is repeated except that the appropriate 1-aryloxy-3-β-(4-mercaptophthalazin-1-yloxyacetamido)ethylamino-2-propanol derivative is used as starting material. There are thus obtained the compounds described in the following table:

| R³ | R⁴ | m.p. (°C.) | crystallisation solvent |
| --- | --- | --- | --- |
| H | H | 175–180 | aqueous dimethylformamide |
| 2-methyl | H | 178–180 | aqueous dimethylformamide |
| 2-chloro | H | 193–196 | aqueous dimethylformamide |
| 4-chloro | H | 192–195 | aqueous dimethylformamide |
| 2-carbamoyl | H | 194–198 | aqueous dimethylformamide |
| 2-methoxy | H | dihydrochloride 181–185 | ethanol |
| 2-trifluoromethyl | H | 188–192 | aqueous dimethylformamide |
| —CH=CH—CH=CH— | | 185–190 | aqueous dimethylformamide |

The 4-mercaptophthalazine derivatives used as intermediates may be obtained by a similar process to that described in the third paragraph of Example 5, except that ethyl 4-mercaptophthalazin-1-yloxyacetate is used as starting material. These intermediates are described in the following table:

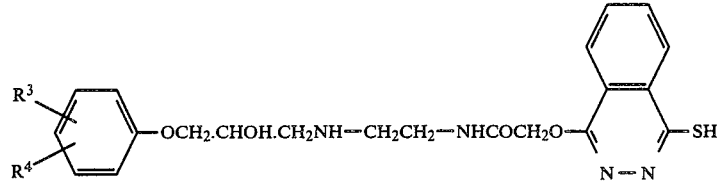

| $R^3$ | $R^4$ | m.p. (°C.) |
|---|---|---|
| H | H | 191–195 |
| 2-methyl | H | 104–118 |
| 2-chloro | H | 118–124 |
| 4-chloro | H | 132–140 |
| 2-carbamoyl | H | 78–82 |
| 2-methoxy | H | 133–140 |
| 2-trifluoromethyl | H | (oil) |
| —CH=CH—CH=CH— | | 145–151 |

Ethyl 4-mercaptophthalazin-1-yloxyacetate may be obtained as follows:

A mixture of ethyl 4-hydroxyphthalazin-1-yloxyacetate (12 g.), phosphorus pentasulphide (14.4 g.) and toluene (200 ml.) is stirred and heated under reflux for 10 minutes, filtered hot and the solid residue is washed with hot toluene. The combined filtrate and washings are evaporated to dryness, the residue is dissolved in chloroform and the mixture is filtered. The filtrate is evaporated to dryness and the solid residue is triturated with ether and then crystallised from ethanol. There is thus obtained ethyl 4-mercaptophthalazin-1-yloxyacetate, m.p. 181°–184° C.

EXAMPLE 7

The process described in Example 5 is repeated except that the appropriate 1-aryloxy-3-β-(4-mercaptophthalazin-1-ylacetamido)ethylamino-2-propanol derivative is used as starting material. There are thus obtained the compounds described in the following table.

| $R^3$ | m.p. (°C.) | crystallisation solvent |
|---|---|---|
| H | (hygroscopic trihydrochloride) | — |
| 2-methyl | 175–178 | ethanol |
| 2-chloro | 170–175 | ethanol |
| 2-carbamoyl | trihydrochloride 120–125 | isopropanol |
| 2-allyl | 118–123 | isopropanol |
| 2-ethyl | hemihydrate 162–167 | methanol/isopropanol |

The 4-mercaptophthalazine derivatives used as intermediates may be obtained by a similar process to that described in the third paragraph of Example 5, except that ethyl 4-mercaptophthalazin-1-ylacetate is used as starting material. These intermediates are described in the following table:

| $R^3$ | m.p. (°C.) |
|---|---|
| H | 176–182 |
| 2-methyl | 180–183 |
| 2-chloro | 175–179 |

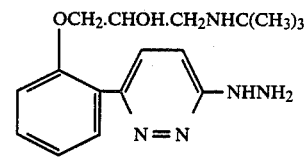

| R³ | m.p. (°C.) |
| --- | --- |
| 2-carbamoyl | 73–83 |
| 2-allyl | 154–158 |
| 2-ethyl | 148–152 |

Ethyl 4-mercaptophthalazin-1-ylacetate, m.p. 155°–158° C. after crystallisation from ethanol, may be obtained from ethyl 4-hydroxyphthalazin-1-ylacetate by a similar process to that described in the last paragraph of Example 6.

EXAMPLE 8

A mixture of 1-phenoxy-3-β-(4-mercaptophthalazine-1-carboxamido)ethylamino-2-propanol (1.7 g.), 100% hydrazine hydrate (2 ml.) and ethanol (50 ml.) is heated under reflux for 1 hour and then evaporated to dryness, and the residue is dissolved in aqueous 2N-hydrochloric acid (20 ml.). The solution is washed with ether, basified to pH 14 and then extracted with chloroform. The extract is washed with water, dried and evaporated to dryness, and the residue is redissolved in chloroform. The solution is treated with carbon and filtered, and to the filtrate is added an excess of a solution of oxalic acid in ether. The mixture is filtered and the solid residue is triturated with isopropanol. There is thus obtained 1-phenoxy-3-β-(4-hydrazinophthalazine-1-carboxamido)ethylamino-2-propanol oxalate, m.p. 90°–95° C. (with decomposition).

The 1-phenoxy-3-β-(4-mercaptophthalazine-1-carboxamido)ethylamino-2-propanol used as starting material may be obtained as follows:

An intimate mixture of 1-phenoxy-3-β-aminoethylamino-2-propanol (4.2 g.) and ethyl 4-mercaptophthalazine-4-carboxylate (2.3 g.) is heated at 95° C. for 1 hour, cooled, powdered and stirred with a mixture of aqueous 2N-hydrochloric acid and ether. The mixture is filtered and there is thus obtained as solid residue 1-phenoxy-3-β-(4-mercaptophthalazine-1-carboxamido)ethylamino-2-propanol hydrochloride, m.p. 232°–236° C., which is used without further purification.

BACKGROUND TO THE INVENTION

A number of compounds are known wherein the hydrazinopyridazine function which characterises the antihypertensive drug hydralazine (which is 1-hydrazinophthalazine), and the 1-amino-3-aryloxypropan-2-ol function which characterises β-adrenergic blocking agents, are both present in the same molecule. Such compounds are described in, for example, United Kingdom Specifications Nos. 1,527,712, 1,548,601 and 1,567,907, European Specification Nos. 7930 and 18016 and Japanese Specification No. 56/169675. None of these specifications discloses the linking of the hydrazinopyridazine function through the amino group of the 1-amino-3-aryloxypropan-2-ol function. One known compound which is under development as an antihypertensive agent is known as PRIZIDOLOL, or SKF92657, and this has the chemical structure:

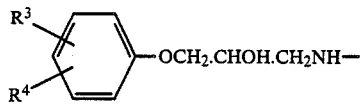

What we claim is:
1. A compound of the formula:

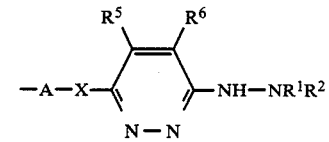

wherein A stands for an alkylene radical of from 2 to 6 carbon atoms, wherein either $R^1$ stands for hydrogen and $R^2$ stands for hydrogen or for an alkoxycarbonyl radical of from 2 to 6 carbon atoms or an aralkoxycarbonyl radical of from 8 to 12 carbon atoms, or $R^1$ and $R^2$ together form an alkylidene radical of from 2 to 6 carbon atoms or an aralkylidene radical of from 7 to 12 carbon atoms, or an alkoxycarbonyl or aralkoxycarbonyl-alkylidene radical of, respectively, from 4 to 10 or from 9 to 15 carbon atoms; wherein $R^3$ and $R^4$, which may be the same or different, each stands for a hydrogen or halogen atom, a hydroxy, amino, nitro, trifluoromethyl, carbamoyl or cyano radical, an alkyl, hydroxyalkyl, cycloalkyl, alkenyl, alkynyl, alkoxy, alkylthio, cycloalkoxy, alkenyloxy, alkynyloxy or alkanoyl radical each of up to 6 carbon atoms, or an aryl, aryloxy or dialkylamino radical each of up to 12 carbon atoms; or wherein $R^3$ and $R^4$ together form the trimethylene, tetramethylene, 1-oxotetramethylene, propylene, but-2-enylene or buta-1,3-dienylene radical such that together with the adjacent benzene ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein $R^5$ and $R^6$, which may be the same or different, each stands for a hydrogen atom or for an alkyl radical of up to 6 carbon atoms, or wherein $R^5$ and $R^6$ together form the buta-1,3-dienylene radical such that together with the adjacent pyridazine ring they form the phthalazinyl radical; and wherein X stands for the oxygen atom; or an acid-addition salt thereof.

2. A compound as claimed in claim 1, wherein A is ethylene, trimethylene, 1-methylethylene, 1,1-dimethylethylene or 1,2-dimethylethylene;
wherein either $R^1$ is hydrogen and $R^2$ is hydrogen or methoxycarbonyl, ethoxycarbonyl or benzyloxycarbonyl;
or $R^1$ and $R^2$ together form ethylidene or 1-methyl-2-benzyloxycarbonylethylidene;
wherein $R^3$ and $R^4$ which may be the same or different, each is hydrogen, fluorine, chlorine, bromine, iodine, hydroxy, amino, nitro, trifluoromethyl, carbamoyl, cyano, methyl, ethyl, n-propyl, hydroxymethyl, 1-hydroxyethyl, cyclopropyl, cyclopentyl, allyl, ethynyl, methoxy, isopropoxy, methylthio, cyclopentyloxy, allyloxy, propargyloxy, formyl, acetyl, phenyl, phenoxy or dimethylamino;
or $R^3$ and $R^4$ together form trimethylene, tetramethylene, 1-oxotetramethylene, propenylene, but-2-enylene or buta-1,3-dienylene;
wherein either $R^5$ and $R^6$, which may be the same or different, each is hydrogen, methyl or ethyl; or wherein $R^5$ and $R^6$ together form buta-1,3-dienylene;
and wherein X has the meaning stated in claim 1;
or an acid-addition salt thereof.

3. A compound as claimed in claim 1 wherein A stands for the ethylene radical, wherein $R^1$ and $R^2$ both stand for hydrogen, wherein $R^3$ stands for a hydrogen or halogen atom or for an alkyl or alkoxy radical each of up to 3 carbon atoms in the orthoposition of the benzene ring and $R^4$ stands for hydrogen, wherein either $R^5$ and $R^6$ both stand for hydrogen atoms or $R^5$ and $R^6$ together form the buta-1,3-dienylene radical, and wherein X stands for the oxygen atom or an acid-addition salt thereof.

4. The compound 1-(2-tolyloxy)-3-β-(6-hydrazinopyridazin-3-yloxy)-ethylamino-2-propanol or an acid-addition salt thereof.

5. A pharmaceutical composition for use in producing an antihypertensive effect comprising as active ingredient at least one compound or an acid-addition salt thereof, claimed in claim 1, in association with a pharmaceutically-acceptable diluent or carrier therefor.

6. A method for producing an antihypertensive effect in a warm-blooded animal in need of such treatment which comprises administering to said animal an effective amount of a compound claimed in claim 1.

7. A composition as claimed in claim 5 which contains, in addition to said compound or acid-addition salt thereof, at least one drug selected from the group consisting of phenobarbitone, meprobamate, chloropromazine, chlordiazepoxide and diazepam, glyceryl trinitrate, pentaerythritol tetranitrate, isosorbide dinitrate, chlorthiazide, reserpine, bethanidine and guanethidine, quinidine, digitalis, propranolol, atenolol and phentolamine.

8. A compound of the formula:

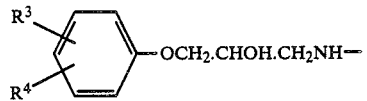

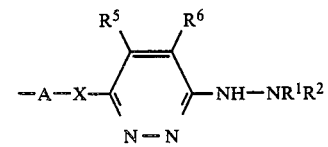

wherein A stands for an alkylene radical of from 2 to 6 carbon atoms, wherein either $R^1$ stands for hydrogen and $R^2$ stands for hydrogen or for an alkoxycarbonyl radical of from 2 to 6 carbon atoms, or $R^1$ and $R^2$ together form an alkylidene radical of from 2 to 6 carbon atoms; wherein $R^3$ and $R^4$, which may be the same or different, each stands for a hydrogen or halogen atom, cyano radical, alkyl, allyl, ethynyl, alkoxy, or allyloxy radical each of up to 6 carbon atoms; wherein $R^5$ and $R^7$ each stands for a hydrogen atom; and wherein X stands for the oxygen atom; or an acid-addition salt thereof.

9. A pharmaceutical composition comprising a compound according to claim 8, and a pharmaceutically acceptable carrier or diluent.

10. A method for the treatment of hypertension which comprises administering an anti-hypertensive amount of a compound as defined in claim 8 to a patient suffering from hypertension.

* * * * *